United States Patent [19]
Foreman

[11] Patent Number: 4,938,755
[45] Date of Patent: Jul. 3, 1990

[54] ABSORBENT ARTICLE HAVING A CONTAINMENT POCKET

[75] Inventor: John H. Foreman, Cincinnati, Ohio

[73] Assignee: The Procter & Gamble Company, Cincinnati, Ohio

[21] Appl. No.: 271,796

[22] Filed: Nov. 15, 1988

Related U.S. Application Data

[63] Continuation of Ser. No. 114,929, Oct. 30, 1987, Pat. No. 4,816,025, which is a continuation of Ser. No. 917,452, Oct. 10, 1986, Pat. No. 4,738,677.

[51] Int. Cl.$^5$ .............................................. A61F 13/16
[52] U.S. Cl. ............................... 604/385.2; 604/385.1
[58] Field of Search ............ 604/378, 381, 382, 385.1, 604/385.2, 389

[56] References Cited

U.S. PATENT DOCUMENTS

| | | |
|---|---|---|
| 2,545,674 | 3/1951 | Ralph . |
| 2,575,164 | 11/1951 | Donovan . |
| 2,916,037 | 12/1959 | Hansen . |
| 3,386,442 | 6/1968 | Sabee . |
| 3,452,753 | 7/1969 | Sanford . |
| 3,530,859 | 9/1970 | Helmowitz . |
| 3,572,342 | 3/1971 | Lindquist et al. . |
| 3,593,716 | 7/1971 | Vogt . |
| 3,658,064 | 4/1972 | Pociluyko . |
| 3,665,920 | 5/1972 | Davis . |
| 3,667,466 | 6/1972 | Ralph . |
| 3,744,494 | 7/1973 | Marsan . |
| 3,771,524 | 11/1973 | Ralph . |
| 3,807,402 | 4/1974 | Miller et al. . |
| 3,825,006 | 7/1974 | Ralph . |
| 3,828,784 | 8/1974 | Zoephel . |
| 3,860,003 | 1/1975 | Buell . |
| 3,920,017 | 11/1975 | Karami . |
| 3,929,134 | 12/1975 | Karami . |
| 3,930,501 | 1/1976 | Shcaar . |
| 3,978,861 | 9/1976 | Schaar . |
| 3,995,640 | 12/1976 | Schaar . |
| 3,999,547 | 12/1976 | Hernandez . |
| 4,040,423 | 8/1977 | Jones, Sr. . |
| 4,041,950 | 8/1977 | Jones, Sr. . |
| 4,090,515 | 5/1978 | Karami . |
| 4,210,143 | 7/1980 | De Jonckheere . |
| 4,326,528 | 4/1982 | Ryan et al. . |
| 4,413,996 | 11/1983 | Taylor . |

(List continued on next page.)

FOREIGN PATENT DOCUMENTS

| | | |
|---|---|---|
| 45217-85 | 2/1986 | Australia . |
| 2561078 | 9/1985 | France . |
| 4118031 | 8/1966 | Japan . |
| 0790062 | 2/1958 | United Kingdom ................ 604/397 |
| 2159693 | 12/1985 | United Kingdom . |
| 2161059 | 1/1986 | United Kingdom . |
| 2193625 | 2/1988 | United Kingdom . |

Primary Examiner—Stephen C. Pellegrino
Assistant Examiner—Sharon Rose
Attorney, Agent, or Firm—Steven W. Miller; John M. Pollaro; Fredrick H. Braun

[57] ABSTRACT

An integral disposable absorbent article such as a diaper provided with an absorbent core; a liquid impervious backsheet; a first barrier cuff disposed adjacent each longitudinal edge of the absorbent article and each having a first proximal edge and a first distal edge; a spacing means for spacing the first distal edge of each of the first barrier cuffs away from the liquid-receiving surface of the absorbent article; and a second barrier cuff disposed adjacent at least one and preferably adjacent each of the end edges of the absorbent article and having a second proximal edge and a second distal edge, the distal edges of the barrier cuffs overlapping at corner points to form a containment pocket. The spacing means preferably comprises a spacing elastic member that extends longitudinally along the first distal edge beyond the second distal edges. Closing means secure together the first distal edges and the second distal edges adjacent the corner points so as to space both the first and second distal edges away from the liquid-receiving surface of the absorbent article. The containment pocket has channels that are formed between the proximal edges and the distal edges because the distal edges of the barrier cuffs are spaced away from the liquid-receiving surface so as to restrain, contain, and hold body exudates.

16 Claims, 1 Drawing Sheet

U.S. PATENT DOCUMENTS

| | | |
|---|---|---|
| 4,490,148 | 12/1984 | Beckestrom . |
| 4,500,316 | 2/1985 | Damico . |
| 4,589,876 | 5/1986 | Van Tilburg . |
| 4,636,207 | 1/1987 | Buell . |
| 4,657,539 | 4/1987 | Hasse . |
| 4,662,877 | 5/1987 | Williams . |
| 4,681,579 | 7/1987 | Toussant et al. . |
| 4,687,478 | 8/1987 | Van Tilburg . |
| 4,695,278 | 9/1987 | Lawson . |
| 4,704,115 | 11/1987 | Buell . |
| 4,704,116 | 11/1987 | Enloe . |
| 4,738,677 | 4/1988 | Foreman . |
| 4,753,646 | 6/1988 | Enloe . |
| 4,795,454 | 1/1989 | Dragoo . |
| 4,808,178 | 2/1989 | Aziz et al. . |
| 4,816,025 | 3/1989 | Foreman . |

ABSORBENT ARTICLE HAVING A CONTAINMENT POCKET

This is a continuation of application Ser. No. 114,929, filed on October 30, 1987, U.S. Pat. No. 4,816,025, which is a continuation of application Ser. No. 917,452 filed on October 10, 1986, U.S. Pat. No. 4,738,677.

FIELD OF THE INVENTION

The present invention relates to absorbent articles such as disposable diapers, and more particularly, to absorbent articles having barrier cuffs so as to improve the containment characteristics of the absorbent article.

BACKGROUND OF THE INVENTION

The major function of absorbent articles such as disposable diapers and adult incontinent briefs is to absorb and contain body exudates. Such articles are thus intended to prevent body exudates from soiling, wetting, or otherwise contaminating clothing or other articles, such as bedding, that come in contact with the wearer. The most common mode of failure for such products occurs when body exudates leak out of the gaps between the article and the wearer's leg or waist to adjacent clothing because they are not immediately absorbed within the article. This is most evident with loose fecal material which is not easily absorbed by the absorbent article and tends to "float" on the liquid-receiving surface of the absorbent article.

Contemporary disposable diapers, such as those disclosed in U.S. Pat. No. 3,860,003 issued to Kenneth Barclay Buell on January 14, 1975, have a topsheet, a backsheet, an absorbent core, and elasticized leg flaps to improve both wearing comfort and the ability to contain body exudates. These elasticized leg flaps prove effective generally to prevent wicking and overflow from the fluid laden diaper to clothing contacting the edges of the diaper in that the elasticized leg flaps present a fluid impervious barrier between the edge of the diaper and the contacting clothing, and in addition, provide a gasketing action about the legs of the wearer. Despite the effectiveness of such structures, however, body exudates, especially loose fecal material, can leak through the elasticized leg flaps and soil the wearer's clothing because the diaper does not constrain the free flow of such material nor provide a structure to hold it within the diaper so that as such material freely floats on the liquid-receiving surface of the diaper, it tends to work its way past the elasticized leg flaps.

Therefore, it is an object of the present invention to provide an absorbent article which has improved containment characteristics.

It is an additional object of the present invention to provide an absorbent article having barrier cuffs which act as a restraint against the leakage of body exudates.

It is a further object of the present invention to provide an absorbent article having a pair of first barrier cuffs and at least one second barrier cuff which interact to form a containment pocket around a portion of the periphery of the absorbent article so as to provide a restraint against the leakage of body exudates, thereby improving the containment characteristics of the absorbent article, especially in regard to loose fecal material.

It is also an object of the present invention to provide an absorbent article having a containment pocket wherein the distal edges are raised above the liquid-receiving surface of the absorbent article when the article is fitted on the wearer such that a channel is formed around the containment pocket which restrains, contains and holds body exudates within the absorbent article.

These and other objects of the present invention will be more readily apparent when considered in reference to the following description and when taken in conjunction with the accompanying drawings.

SUMMARY OF THE INVENTION

In accordance with the present invention, an integral disposable absorbent article such as a diaper is provided with an absorbent core having a garment surface and a body surface; a liquid impervious backsheet positioned adjacent the garment surface of the absorbent core; a first barrier cuff disposed adjacent each longitudinal edge of the absorbent article and each having a first proximal edge and a first distal edge; a spacing means associated with each of said first barrier cuffs for spacing the first distal edge of each of the first barrier cuffs away from the liquid-receiving surface of the absorbent article; and a second barrier cuff disposed adjacent at least one and preferably adjacent each of the end edges of the absorbent article and having a second proximal edge and a second distal edge, the distal edges of the barrier cuffs overlapping at corner points to form a containment pocket. The spacing means preferably comprises a spacing elastic member that extends longitudinally along the first distal edge beyond the second distal edges. In addition, closing means secure together the first distal edges and the second distal edges adjacent the corner points so as to space both the first and second distal edges away from the liquid-receiving surface of the absorbent article. The containment pocket has channels that are formed between the proximal edges and the distal edges because the distal edges of the barrier cuffs are spaced away from the liquid-receiving surface so as to restrain, contain, and hold body exudates.

Leakage prevention is enhanced because body exudates which are not immediately absorbed by the absorbent core, typically loose fecal material and gushes of urine, contact the barrier cuffs and are contained and held within the channels of the containment pocket so that exudates do not leak out of the diaper at the gaps between the diaper and the legs or waist of the wearer. Additionally, should such exudates flow beyond the barrier cuffs, leakage prevention may be further enhanced by gasketing cuffs positioned adjacent the barrier cuffs to form an additional fluid impervious barrier about the leg or waist of the wearer.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

Figure 1:
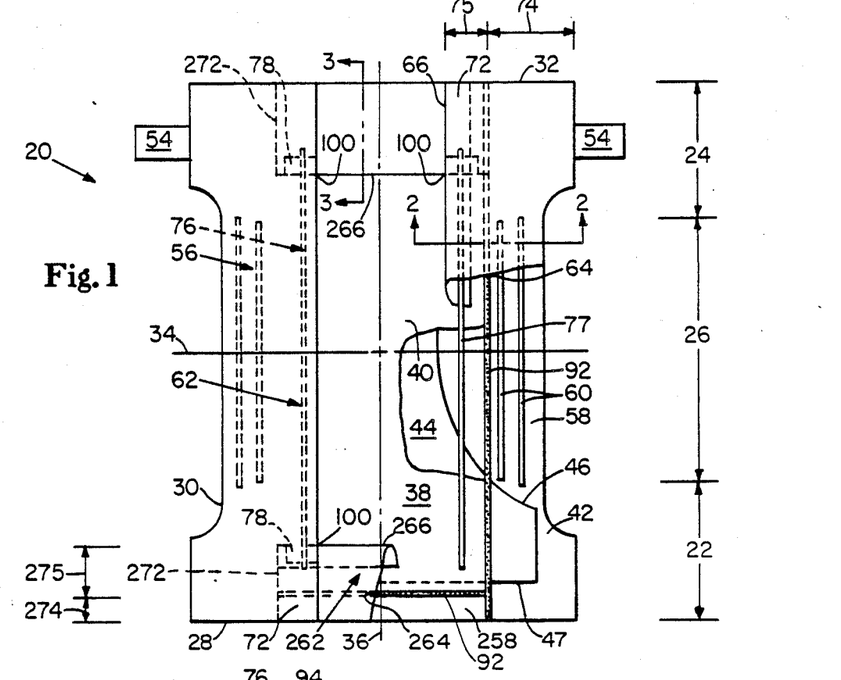
FIG. 1 is a plan view of a disposable diaper embodiment of the present invention having portions cut away to reveal underlying structure.

As used herein, the term "integral disposable absorbent article" refers to articles which absorb and contain body exudates and more specifically refers to articles which are placed against or in proximity to the body of the wearer to absorb and contain the various exudates discharged from the body, which are intended to be discarded after a single use (i.e., they are not intended to be laundered or otherwise restored or reused), and which are unitary in that they do not require separate manipulative parts like a separate holder and liner. A preferred embodiment of the integral disposable absorbent article of the present invention, diaper 20, is shown in FIG. 1. As used herein, the term "diaper" refers to a garment generally worn by infants and incontinent persons that is worn about the lower torso of the wearer. It should be understood, however, that the present invention is also applicable to other integral disposable absorbent articles such as incontinent briefs and the like.

FIG. 1 is a plan view of the diaper 20 of the present invention in its flat-out, uncontracted state (i.e., with all elastic induced contraction pulled out) with portions of the structure being cut-away to more clearly show the construction of the diaper 20 and with the portion of the diaper 20 which contacts the wearer facing the viewer. The diaper 20 is shown in FIG. 1 to have a front waist region 22, a back waist region 24, a crotch region 26 and a periphery 28 which is defined by the outer edges of the diaper 20 in which the longitudinal edges are designated 30 and the end edges are designated 32. The diaper 20 additionally has a lateral centerline which is designated 34 and a longitudinal centerline which is designated 36.

The diaper 20 comprises a liquid pervious topsheet 38, the liquid-receiving surface of the diaper 20 being generally defined by the topsheet 38 and being designated 40; a liquid impervious backsheet 42; an absorbent core 44 having side edges 46 and waist edges 47 and comprising an absorbent layer 48 and first and second tissue layers 50 and 52, respectively; a pair of tape-tab fasteners 54; gasketing cuffs 56 each comprising a side flap 58 and one or more flap elastic members 60; first barrier cuffs 62 each comprising a flap portion 74 and a channel portion 75 and having a first proximal edge 64, a first distal edge 66, an inboard surface 68, an outboard surface 70, and ends 72; spacing means 76 such as a spacing elastic member 77 for spacing the first distal edge 66 away from the liquid-receiving surface 40; and second barrier cuffs 262 each comprising a second flap portion 274 and a second channel portion 275 and having a second proximal edge 264, a second distal edge 266, an inner surface 268, an outer surface 270, and ends 272. As shown in FIG. 1, the spacing elastic members 77 preferably extend longitudinally along the first distal edges 66 beyond the second distal edges 266 so as to space not only the first distal edges 66 but also the second distal edges 266 away from the liquid-receiving surface 40 and to eliminate the need and expense of positioning a second spacing means in the second barrier cuffs 262. The diaper 20 additionally comprises closing means 78 such as an adhesive bead for securing the distal edges with each other. While the topsheet 38, the absorbent core 44, the backsheet 42, and the gasketing cuffs 56 may be assembled in a variety of well known configurations, a preferred diaper configuration is described generally in U.S. Pat. No. 3,860,003 entitled "Contractable Side Portions for Disposable Diaper", which issued to K. B. Buell on January 14, 1975, and which patent is incorporated herein by reference.

FIG. 1 shows a preferred embodiment of the diaper 20 in which the backsheet 42 has length and width dimensions generally larger than those of the absorbent core 44. The backsheet 42 extends beyond the edges of the absorbent core 44 to thereby form the periphery 28 of the diaper 20. The periphery 28 defines the outer perimeter or, in other words, the edges of the diaper 20. The periphery 28 comprises the end edges 32 and the longitudinal edges 30.

The diaper 20 has front and back waist regions 22 and 24 extending, respectively, from the end edges 32 of the diaper periphery 28 toward the lateral centerline 34 of the diaper 20 a distance from about ¼ to about ⅓ the length of the diaper 20. The waist regions comprise those portions of the diaper 20 which, when worn, encircle the waist of the wearer. The crotch region 26 is that portion of the diaper 20 between the waist regions 22 and 24, and comprises that portion of the diaper 20 which, when worn, is positioned between the legs of the wearer and covers the lower torso of the wearer.

Figure 2:
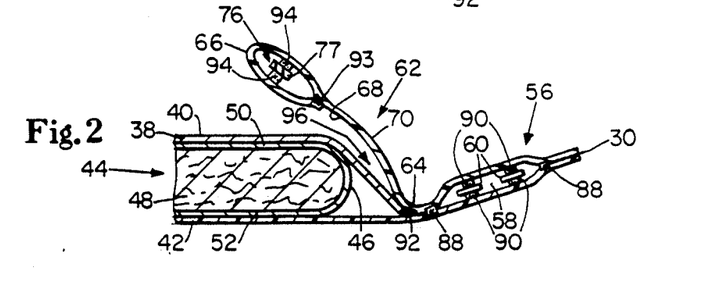
FIG. 2 is a fragmentary sectional view taken along section line 2—2 of FIG. 1.

FIG. 2 is a fragmentary sectional view taken along line 2—2 of FIG. 1 and depicts a preferred diaper construction in the crotch region 26 of the diaper 20. The absorbent core 44 comprises the absorbent layer 48 that is shown as being completely enveloped by the first and second tissue layers 50 and 52 which define the garment surface and the body surface of the absorbent core 44. The absorbent core 44 is disposed between the topsheet 38 and the backsheet 42; the backsheet 42 extending beyond the side edge 46 of the absorbent core 44. The first barrier cuff 62 is formed by affixing portions of a separate first barrier cuff member to the backsheet 42 adjacent the longitudinal edge 30 of the diaper 20 with attachment means 88 such as adhesive; a leakage-resistant seal being formed by the attachment means 88, the first barrier cuff 62 and the backsheet 42. This flap portion 74 of the first barrier cuff 62 and the backsheet 42 define the side flap 58 and enclose the flap elastic members 60 adjacent the longitudinal edge 30. The flap elastic members 60 are secured in the first barrier cuff-backsheet-formed side flap 58 by flap elastic attachment means 90. The elastically contractible gasketing cuff 56 is thereby formed by the side flap 58 and the flap elastic members 60. A channel portion 75 of the first barrier cuff 62 is contiguous with the flap portion 74 and comprises the first proximal edge 64 and the first distal edge 66. The first proximal edge 64 of the first barrier cuff 62 is formed inboard of the gasketing cuff 56, preferably between the flap elastic members 60 and the side edge 46 of the absorbent core 44, by adjoining a segment of the first barrier cuff member to the backsheet 42 by the edge attachment means 92 such as an adhesive bead so as to form a leakage-resistant seal along the first proximal edge 64. The first distal edge 66 is disposed inboard of the first proximal edge 64 and is not secured to any underlying elements of the diaper 20. As shown in FIG. 2, the first distal edge 66 is formed by folding the end of the first barrier cuff member back upon itself and securing it to another segment of the first barrier cuff member by the distal attachment means 93 to form a tunnel. A spacing means 76 such as a spacing elastic member 77 is enclosed in the tunnel that is formed when the end of the first barrier cuff member is folded back upon itself; the spacing elastic member 77 being secured in the first barrier cuff 62 by the spacing elastic attachments means 94. The first distal edge 66 is thus spaced away from the liquid-receiving surface 40 by the elastic gathering action of the spacing elastic members 77; a channel 96 thereby being formed by at least the first proximal edge 64, the first distal edge 66 and the inboard surface 68 of the first barrier cuff 62. The channel 96 is shown as being open and ready to restrain, contain and hold body exudates until the diaper 20 is removed from the wearer. The topsheet 38 is positioned adjacent the body surface of the absorbent core 44 and extends beyond the side edge 46 of the absorbent core 44 and terminates inwardly and preferably adjacent the first proximal edge 64, where it is preferably secured with the side flap 58 (backsheet 42) and the first proximal edge 64 by the edge attachment means 92 to provide a leakage-resistant seal along the first proximal edge 64.

Figure 3:
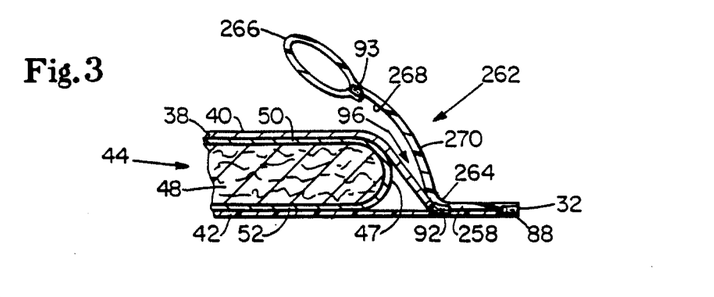
FIG. 3 is a fragmentary sectional view taken along section line 3—3 of FIG. 1.

FIG. 3 is a fragmentary sectional view taken along line 3—3 of FIG. 1 and depicts a preferred diaper construction in the back waist region 24 of the diaper 20. The absorbent core 44 comprises the absorbent layer 48 that is shown as being completely enveloped by the first and second tissue layers 50 and 52 which define the garment surface and the body surface of the absorbent core 44. The absorbent core 44 is disposed between the topsheet 38 and the backsheet 42; the backsheet 42 extending beyond the waist edge 47 of the absorbent core 44. The second barrier cuff 262 is formed by affixing portions of a separate second barrier cuff member to the backsheet 42 adjacent the end edge 32 of the diaper 20 with attachment means 88 such as an adhesive; a leakage-resistant seal being formed by the attachment means 88, the second barrier cuff 262 and the backsheet 42. This second flap portion 274 of the second barrier cuff 262 and the backsheet 42 define the waist flap 258. (In the preferred embodiment shown in FIG. 3, a second gasketing cuff is not formed along the waist flap 258 although such a configuration is contemplated.) A second channel portion 275 of the second barrier cuff 262 is contiguous with the second flap portion 274 and comprises the second proximal edge 264 and the second distal edge 266. The second proximal edge 264 and the second barrier cuff 262 is formed outboard of the waist edge 47 of the absorbent core 44, between the waist edge 47 and the end edge 32, by adjoining a segment of the second barrier cuff member to the backsheet 42 by the edge attachment means 92 such as an adhesive bead so as to form a leakage-resistant seal along the second proximal edge 264. The second distal edge 266 is disposed inboard of the second proximal edge 264 and is not secured to any underlying elements of the diaper 20. Although a spacing means 76 is preferably not disposed in the second barrier cuff 262, the second distal edge 266 is preferably formed by folding the end of the second barrier cuff member back upon itself and securing it to another segment of the second barrier cuff member by the distal attachment means 93 to form a tunnel. (While the second distal edge 266 is preferably formed as above so as to present a soft nonjagged edge to the wearer, alternative methods of forming the second distal edge 266 as well as the first distal edges 66 are within the scope of the invention.) A spacing means 76 such as a spacing elastic member 77 is preferably not disposed in the second barrier cuff 262 because the gathering action of the spacing elastic member 77 along the first distal edge 66 raises both the first and second distal edge above the liquid-receiving surface 40 to form a channel 96; however, in alternative embodiments such a construction is contemplated. The topsheet 38 is positioned adjacent the body surface of the absorbent core 44 and preferably extends beyond the waist edge 47 of the absorbent core 44 and terminates inwardly and preferably adjacent the second proximal edge 264, where it is preferably secured with the waist flap 258 (backsheet 42) and the second proximal edge 264 by the edge attachment means 92 to provide a leakage-resistant seal along the second proximal edge 264.

As shown in FIG. 1, the first distal edges 66 of the first barrier cuffs 62 and the second distal edges 266 of the second barrier cuffs 262 overlap at at least four points or areas which are designated corner points 100. While the distal edges may be disposed to overlap at only points, it is desirable that the distal edges overlap along a line at each intersection zone, most preferably along two lines (as is shown in FIG. 1) so that the barrier cuffs overlap completely adjacent the corners of the diaper 20. The distal edges are secured with each other adjacent the corner points 100 by the closing means 78 so as to integrate the movement of the barrier cuffs and prevent their inversion during use. A leakage-resistant seal also preferably extends around the entire diaper 20 along the edges of the diaper 20 and the proximal edges to insure that exudates may not leak out along the periphery 28 of the diaper 20. The overlapping barrier cuffs thus in this preferred embodiment provide a containment pocket around the entire periphery 28 of the diaper 20 formed by the channels 96 of each of the barrier cuffs.

The topsheet 38 is substantially noncoterminous with the backsheet 42 so that liquids will not wick through the topsheet 38 underneath and beyond the proximal edges of the barrier cuffs, thereby reducing the leakage of liquids out of the diaper 20. The topsheet 38 is positioned adjacent the body surface of the absorbent core 44 and overlays a major portion of the absorbent core 44 so that exudates are discharged onto the topsheet 38 and penetrate through the topsheet 38 where they are absorbed by the absorbent core 44. The topsheet 38 extends outwardly toward the edges of the absorbent core 44 so that a major portion of the absorbent core 44 is disposed between the backsheet 42 and the topsheet 38. In the preferred embodiment shown in FIG. 1, the topsheet 38 has length and width dimensions generally larger than those of the absorbent core 44. The topsheet 38 preferably extends toward the edges of the absorbent core 44, preferably beyond the side edges 46 in at least the crotch region 26 and the waist edges 47, wherein the topsheet 38 preferably terminates inwardly of the proximal edges of the barrier cuffs. Inwardly is used herein to denote configurations wherein the terminating edge of the topsheet 38 is positioned adjacent the proximal edge (i.e., the topsheet 38 is substantially coterminous with the proximal edge) and configurations wherein the terminating edge of the topsheet 38 is positioned remotely from and inboard of the proximal edge. Adjacent is used in this context to mean that the topsheet terminates at the proximal edge, plus or minus small areas of topsheet material that may extend inside or beyond the proximal edges due to machine tolerances during manufacture or variations in the topsheet's area when it is manufactured. In the most preferred embodiments as shown in FIG. 1, the topsheet 38 is positioned adjacent the proximal edges and is secured to the flaps (backsheet 42) adjacent to the proximal edges by the edge attachment means 92 so as to form a leakage-resistant seal along the proximal edges around the periphery 28 of the diaper 20.

The topsheet 38 is compliant, soft feeling, and non-irritating to the wearer's skin. Further, the topsheet 38 is liquid pervious permitting liquids to readily penetrate through its thickness. A suitable topsheet may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and synthetic fibers. Preferably, it is made of a hydrophobic material to isolate the wearer's skin from liquids in the absorbent core 44.

A preferred topsheet 38 comprises staple length polypropylene fibers having a denier of about 1.5, such as Hercules Type 151 polypropylene marketed by Hercules, Inc. of Wilmington, Delaware. As used herein, the term "staple length fibers" refers to those fibers having a length of at least about 15.9 mm (0.625 inches).

There are a number of manufacturing techniques which may be used to manufacture the topsheet 38. For example, the topsheet 38 may be woven, non-woven, spunbonded, carded, or the like. A preferred topsheet 38 is carded, and thermally bonded by means well known to those skilled in the fabrics art. Preferably, the topsheet 38 has a weight from about 18 to about 25 grams per square meter, a minimum dry tensile strength of at least about 400 grams per centimeter in the machine direction and a wet tensile strength of at least about 55 grams per centimeter in the cross machine direction.

The absorbent core 44 may be any means which is generally compressible, conformable, non-irritating to the wearer's skin, and capable of absorbing and retaining liquids and certain body exudates. A preferred absorbent core 44 has first and second opposed faces (a body surface and a garment surface) and comprises an absorbent layer 48 and first and second tissue layers 50 and 52, respectively. The first and second tissue layers 50 and 52 overlay the major surfaces of the absorbent layer 48 to form the garment surface and the body surface of the absorbent core 44.

The absorbent layer 48 may be manufactured in a wide variety of sizes and shapes (e.g., rectangular, hourglass, etc.) and from a wide variety of liquid absorbent materials commonly used in disposable diapers and other absorbent articles, such as comminuted wood pulp which is generally referred to as airfelt. Examples of other suitable absorbent materials include creped cellulose wadding, absorbent foams, absorbent sponges, super absorbent polymers, absorbent gelling materials, or any equivalent materials or combination of materials. The total absorbent capacity of the absorbent layer 48 should, however, be compatible with the design exudate loading in the intended use of the diaper 20. Further, the size and absorbent capacity of the absorbent layer 48 may be varied to accommodate wearers ranging from infants through adults.

A preferred embodiment of the diaper 20 has an hourglass-shaped absorbent layer 48 and is intended to be worn by infants ranging in weight from about 5 kgs to about 12 kgs (about 12 pounds to about 26 pounds). The airfelt used in the absorbent layer 48 weighs from about 30 grams to about 56 grams, has a generally uniform caliper, and has an absorbent capacity of from about 8 grams to about 16 grams of water per gram of absorbent material. It should be understood, however, that the size, shape, configuration, and total absorbent capacity of the absorbent layer 48 may be varied to accommodate wearers ranging from infants through adults.

Therefore, the dimensions, shape, and configuration of the absorbent layer 48 may be varied (e.g., the absorbent layer may have a varying caliper, or a hydrophillic gradient, or may contain absorbent gelling materials). The absorbent layer 48 is preferably a batt of airfelt about 32 cm wide (lateral dimension), about 45 cm long (longitudinal dimension) and approximately 7 cm across the narrowest part of the crotch region.

The first and second tissue layers 50 and 52 improve the tensile strength of the absorbent core 44 and reduce the tendency of the absorbent layer 48 to split, lump or ball when wetted. The first and second tissue layers 50 and 52 also help to improve lateral wicking of the absorbed exudates, thereby providing a more even distribution of the exudates throughout the absorbent layer 48. While a number of materials and manufacturing techniques may be used to manufacture the first and second tissue layers 50 and 52, satisfactory results have been obtained with sheets of tissue paper having a basis weight of about 16 grams per square meter (10 lbs. per 3000 square feet) and having an air permeability of about 30.5 cubic meters per minute per square meter (100 cubic feet per minute per square foot) at a pressure differential of about 12.8 millimeters of water ($\frac{1}{2}$ inch). While the first and second tissue layers 50 and 52 are preferably coterminous with the absorbent layer 48, they may have different dimensions, a different configuration, or they may be omitted entirely.

The backsheet 42 is positioned adjacent the garment surface of the absorbent core 44 and is preferably attached thereto by attachments means (not shown) such as those well known in the art. For example, the backsheet 42 may be secured to the absorbent core 44 by a uniform continuous layer of adhesive, a patterned layer of adhesive, or an array of separate lines or spots of adhesive. Adhesives which have been found to be satisfactory are manufactured by Eastman Chemical Products Company of Kingsport, Tennessee and marketed under the tradename Eastobond A-3 and by Century Adhesives, Inc. of Columbus, Ohio and marketed under the tradename Century 5227.

The backsheet 42 is impervious to liquids and is preferably manufactured from a thin plastic film, although other flexible liquid impervious materials may also be used. The backsheet 42 prevents the exudates absorbed and contained in the absorbent core 44 from wetting articles which contact the diaper 20 such as bedsheets and undergarments. Preferably, the backsheet 42 is a polyethylene film having a thickness of from about 0.012 mm (0.5 mil) to about 0.051 cm (2.0 mils), although other flexible, liquid impervious materials may be used. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The backsheet 42 is preferably embossed and/or matte finished to provide a more clothlike appearance. Further, the backsheet 42 may permit vapors to escape from the absorbent core 44 while still preventing exudates from passing through the backsheet 42.

The size of the backsheet 42 is dictated by the size of absorbent core 44 and the exact diaper design selected. In a preferred embodiment, the backsheet 42 has a modified hourglass shape extending beyond the absorbent core 44 a minimum distance of at least about 1.3 cm to about 2.5 cm (about 0.5 to about 1.0 inch) around the entire diaper periphery 28.

Tape tab fasteners 54 are typically applied to the back waist region 24 of the diaper 20 to provide a fastening means to hold the diaper on the wearer. The tape tab fasteners 54 can be any of those well known in the art, such as the fastening tape disclosed in U.S. Pat. No. 3,848,594 issued to K. B. Buell on November 19, 1974, which is incorporated herein by reference. These tape tab fasteners 54 or other diaper fastening means, such as pins, are typically applied near the top edge of a diaper in its "in-use" configuration.

The elastically contractible gasketing cuffs 56 are disposed adjacent the periphery 28 of the diaper 20, preferably adjacent each first barrier cuff 62 along each longitudinal edge 30 so that the gasketing cuffs 56 tend to draw and hold the diaper 20 against the legs of the wearer. Alternatively, a second gasketing cuff may be disposed adjacent either or both of the second barrier cuffs 262 along the end edges 32 of the diaper 20 to provide a waistcuff. While the gasketing cuffs may comprise any of several means as are well known in the diaper art, a particularly preferred gasketing cuff construction comprises a flexible flap and one or more flap elastic members 60, as is described in detail in the hereinbefore referenced U.S. Pat. No. 3,860,003. In addition, a method and apparatus suitable for manufacturing a disposable diaper having elastically contractible gasketing cuffs are described in U.S. Pat. No. 4,081,301 entitled "Method and Apparatus for Continuously Attaching Discrete, Stretched Elastic Strands to Predetermined Isolated Portions of Disposable Absorbent Articles" which issued to K. B. Buell on March 28, 1978 and which patent is incorporated herein by reference. A particularly preferred second gasketing cuff or waistband construction is described in U.S. Pat. No. 4,515,595 entitled "Disposable Diapers With Elastically Contractible Waistbands" which issued to D. J. Kievet and T. F. Osterhage on May 7, 1985 and which patent is incorporated herein by reference.

The flaps should be highly flexible and thus contractible so that the flap elastic members 60 may gather the flaps to provide a gasketing cuff about the legs or waist of the wearer. The flaps are that portion of the diaper 20 between the periphery 28 and the side edges 46 or the waist edges 47 of the absorbent core 44. Thus in a preferred embodiment of the present invention as shown in FIG. 1, the side flaps 58 are formed from the extension of the backsheet 42 and the flap portion 74 of the first barrier cuffs 62 from and along the side edges 46 of the absorbent core 44 of the diaper 20 in at least the crotch region 26 and the waist flaps 258 are formed from the extension of the backsheet 42 and the second flap portion 274 of the second barrier cuffs 262 from and along the waist edges 47 of the absorbent core 44.

The flap elastic members 60 are operatively associated with the flaps in an elastically contractible condition so that in a normally unrestrained configuration, the flap elastic members 60 effectively contract or gather the flaps. The flap elastic members 60 can be associated with the flaps in an elastically contractible condition in at least two ways. For example, the flap elastic members 60 may be stretched and secured to the flaps while the flaps are in an uncontracted condition. Alternatively, the flaps may be contracted, for example by pleating, and the flap elastic members 60 secured to the contracted flaps while the flap elastic members 60 are in their unrelaxed or unstretched condition.

In the embodiment illustrated in FIG. 1, the flap elastic members 60 extend essentially the entire length of the side flaps 58 in the crotch region 26 of the diaper 20. Alternatively, the flap elastic members 60 may extend the entire length of the diaper 20, or any other length suitable to provide an elastically contractible gasketing cuff. The length of the flap elastic members 60 is dictated by the diaper's design.

As shown in FIG. 2, the flap elastic members 60 are operatively associated with the side flaps 58 by securing them to the side flaps 58 with flap elastic attachments means 90. The flap elastic attachment means 90 should be flexible and of sufficient adhesiveness to hold the flap elastic member 60 in its stretched condition. The flap elastic attachment means 90 herein are preferably glue beads made of hot melt adhesives such as marketed by Findley Adhesives Incorporated, Elm Grove, Wisconsin as Findley Adhesives 581, although the flap elastic members 60 may be affixed to the diaper 20 in any of several other ways which are well known in the art. For example, the flap elastic members 60 may be ultrasonically bonded or heat/pressure sealed into the diaper 20 using a variety of bonding patterns or the flap elastic members 60 may simply be glued to the diaper 20. A more detailed description of the manner in which the flap elastic members 60 may be positioned and secured to the diaper 20 can be found in U.S. Pat. No. 4,253,461 issued to Strickland and Visscher on March 3, 1981, and U.S. Pat. No. 4,081,301 issued to Buell on March 28, 1978, both of which are incorporated herein by reference.

One flap elastic member 60 which has been found to be suitable is an elastic strand having a cross section of 0.18 mm by 1.5 mm and made from natural rubber as available from Easthampton Rubber Thread Company of Stewart, Virginia, under the trademark L-1900 Rubber Compound. Other suitable flap elastic members 60 can be made from natural rubber, such as elastic tape sold under the trademark Fulflex 9411 by Fulflex Company of Middletown, Rhode Island. The flap elastic member 60 may also comprise any heat shrinkable elastic material as is well known in the art. Other suitable flap elastic members 60 may comprise a wide variety of materials as are well known in the art including elastomeric films, polyurethane films, elastomeric foams, and formed elastic scrim.

In addition, the flap elastic members 60 may take a multitude of configurations. For example, the width of the flap elastic members 60 may be varied from about 0.25 mm (0.01 inches) to about 25 mm (1.0 inch) or more; the flap elastic members 60 may comprise a single strand of elastic material or may comprise several parallel or non-parallel strands of elastic material; or the flap elastic members 60 may be rectilinear or curvilinear.

The barrier cuffs provide a barrier to restrain the free flow of body exudates along the liquid-receiving surface 40 and provide a structure to hold and contain such exudates within the diaper 20. Each of the barrier cuffs is a flexible member having a proximal edge, a distal edge, an inboard surface, an outboard surface, and ends. As used herein, the term "flexible" refers to materials which are compliant and will readily conform to the general shape and contours of the body. In addition, if the spacing means 76 comprises one or more spacing elastic members 77, the barrier cuffs must be contractible so that the distal edges may be sufficiently spaced away from the liquid-receiving surface 40 so that the channel 96 formed along the barrier cuffs is open to constrain, retain and hold body exudates within the diaper 20. The barrier cuffs may be manufactured from a wide variety of materials such as polypropylene, polyester, rayon, nylon, foams, plastic films, formed films, and elastic foams. A number of manufacturing techniques may be used to manufacture the barrier cuffs. For example, the barrier cuffs may be woven, nonwoven, spunbonded, carded, or the like. A particularly preferred barrier cuff comprises a polypropylene material containing no finish or surfactant to render it liquid impermeable. A particularly preferred polypropylene material is manufacturered by Crown Zellerbach Company as Celestra.

Referring to FIGS. 1, 2 and 3, it can be seen that each of the barrier cuffs preferably has a flap portion and a channel portion. The flap portion is contiguous with the channel portion and extends outwardly from the proximal edge of the channel portion toward the edge of the diaper 20, preferably to the edge, such that each of the flaps is formed from the extension of the backsheet 42 and the flap portion of the respective barrier cuff.

While the flap portion is preferably a continuous segment of the barrier cuff member, the flap portion may be formed from a different piece of material secured to the channel portion of the barrier cuff. Thus, the flap portion may have different physical properties, dimensions, and characteristics than the channel portion. For example, the flap portion need not be liquid impermeable nor extend outwardly to the edge of the diaper 20. In addition, the barrier cuff need not have a flap portion such that a flap portion may be omitted entirely. The flap portion is, however, preferably hydrophobic, liquid impermeable, compliant, soft feeling and non-irritating to the wearer's skin since it contacts the legs of the wearer when in use. The channel portion of the barrier cuffs comprises that portion of the barrier cuff between the proximal edge and the distal edge and generally defines the channel 96 formed along the diaper 20.

As shown in FIGS. 1 and 2, the first barrier cuffs 62 are disposed adjacent each longitudinal edge 30 of the diaper 20 and are preferably disposed adjacent to an inboard of the gasketing cuffs 56; the first proximal edges 64 being preferably disposed inboard of the flap elastic members 60 of the gasketing cuffs 56. The term "inboard" is defined as the direction toward the centerline (34 or 36, respectively) of the diaper 20 that is parallel to the respective edge of the diaper 20 along which the particular gasketing cuff is disposed. The first proximal edge 64 is preferably disposed inboard of the gasketing cuff 56, the flap elastic member 60, so that exudates, especially loose fecal material which is not easily absorbed and tends to float along the liquid-receiving surface 40, will contact the channel portion 75 of the first barrier cuff 62 before it can contact the gasketing cuff 56. The first barrier cuffs 62 are disposed adjacent the gasketing cuffs 56 to provide a more effective dual restraint against the flow of body exudates. The first proximal edge 64 is preferably disposed between the flap elastic member 60 of the gasketing cuff 56 and the longitudinal centerline 36 of the diaper 20. Most preferably, the first proximal edge 64 is disposed between the innermost flap elastic member 60 and the side edge 46 of the absorbent core 44 in at least the crotch region 26 of the diaper 20.

A second barrier cuff 262 is disposed adjacent at least one of the end edges 32 of the diaper 20 and preferably adjacent each of the end edges 32. If a single second barrier cuff 262 is present in the diaper 20, it may be positioned in either the front waist region 22 or the back waist region 24. A second barrier cuff 262 positioned in the back waist region 21 is especially effective in containing loose fecal material while a second barrier cuff 262 disposed in the front waist region 22 is especially effective in containing gushes of urine from male wearers. A second barrier cuff 262 is preferably disposed adjacent each end edge 32 to provide both advantages and to form a containment pocket around the entire periphery 28 of the diaper 20. The second proximal edge 264 of each second barrier cuff 262 is preferably disposed between the end edges 32 of the diaper 20 and the lateral centerline 34. Most preferably, the second proximal edge 264 is disposed outboard of the waist edge 47 of the absorbent core 44. (It should be understood that if a second gasketing cuff is present in a particular embodiment, then the placement of the second barrier cuffs 262 with respect to the second gasketing cuffs is preferably the same as the placement of the first barrier cuffs 62 with respect to the gasketing cuffs 56.) As shown in FIG. 1, the second barrier cuffs 262 extend along only a portion of the end edges 32, between preferably the first proximal edges 64, so as to conserve fabric and for ease of manufacture. However, the second barrier cuffs 262 may alternatively extend along the entire end edge 32 or any fraction thereof at least between the first distal edges 66 to provide a containment pocket.

The proximal edges and the distal edges are in spaced relation to each other and define the effective width of each of the barrier cuffs. The proximal and distal edges may be in a parallel, nonparallel, rectilinear or curvilinear relationship. In addition, each of the barrier cuffs may have a variety of different cross-sectional areas including circular, square, rectangular or any other shape such as that shown in FIGS. 2 and 3. Preferably, the proximal edges are spaced from the distal edges in a parallel and rectilinear relationship to provide barrier cuffs having uniform effective widths. Each barrier cuff preferably has an effective width of at least about 5 mm, and preferably of at least from about 10 mm to about 50 mm.

The distal edges are preferably disposed inboard of the proximal edges to present a more effective barrier against the flow of exudates. The distal edges are maintained inboard of the proximal edges by the closing means 78 so as to obviate their inversion. While the distal edges may alternatively be disposed in other positions in relation to the proximal edges, such positions are not preferred.

The first distal edges 66 are preferably not secured to any other element in at least the crotch region 26 of the diaper 20 so that they may be spaced away from the liquid-receiving surface 40. The second distal edges 266 are preferably not secured to any other element between at least the first distal edges 66 so that they may be spaced away from the liquid-receiving surface 40. The distal edges are preferably spaced away from the liquid-receiving surface 40 so that the barrier cuffs may form a channel 96 to enhance the containment of the diaper 20. As used herein, "spaced" includes embodiments wherein the distal edges may assume one or more positions relative to the liquid-receiving surface 40 including at some times assuming a position adjacent the liquid-receiving surface 40. The distance between a distal edge to the liquid-receiving surface 40 is measured along a line drawn from the distal edge to the closest part of the liquid-receiving surface 40 when the distal edge is positioned so as to be spaced away from the liquid-receiving surface 40 as far as possible. (i.e., in the elastically contracted position). Preferably, the first distal edges 66 are spaced away from the liquid-receiving surface 40 by a height of at least about 2 mm, and more preferably of at least from about 5 mm (about 1/4") to about 10 mm (3/8").

A channel 96 is formed at least along the proximal and distal edges and the inboard surface of each of the barrier cuffs. The channel 96 forms a barrier to the flow of exudates as they tend to move or float across the topsheet 38. Thus, the channel 96 restrains, contains and holds exudates within the diaper 20 until the diaper 20 can be removed.

The barrier cuffs are preferably hydrophobic and more preferably liquid impermeable so as to prevent the strikethrough of body exudates. A liquid impermeable barrier cuff retards the movement of liquid through the barrier cuff, thereby making it more leakage resistant. The barrier cuffs may be rendered liquid impermeable in any manner well known in the art such as selectively treating the barrier cuffs, untreating the barrier cuffs, or by securing a separate material to the barrier cuffs.

The barrier cuffs may additionally be provided with absorbent means secured to or within the barrier cuff. The absorbent means absorb and contain exudates which contact the barrier cuff. The absorbent means may be any means which is capable of absorbing and retaining fluids and may have any size, shape, configuration or absorbent capacity. The absorbent means may be secured to the barrier cuff along the inner surface or within the barrier cuff. Preferably, the absorbent means is a layer of airfelt secured along the inner surface of the barrier cuff and secured along the entire length and width of the inner surface of the barrier cuff.

A preferred embodiment of the diaper 20 shown in FIG. 1 is provided with each of the barrier cuffs joined to the flaps (i.e., the backsheet 42). The term "joined" includes any means for affixing the barrier cuffs to the diaper 20, and includes embodiments wherein the barrier cuffs are separate members directly or indirectly adjoined to the flaps (i.e., integral) or embodiments wherein the barrier cuffs are constructed from the same member or material as an element of the diaper 20 so that the barrier cuffs are a continuous and undivided element of the flaps (i.e., unitary). The barrier cuffs may alternatively be joined to the backsheet 42, the absorbent core 44, the topsheet 38 or any combination of these or other elements of the diaper 20. In a preferred embodiment, the barrier cuffs are integral with the flaps, the first barrier cuffs 62 being integral with the side flaps 58 and the second barrier cuffs 262 being integral with the waist flaps 258. The integral barrier cuffs are thus preferably formed by a single separate strip of material with an intermediate segment adjoined to the flaps by the edge attachment means 92 such as an adhesive to form the proximal edge, the distal edge being formed by folding an end of the material back upon itself and being secured to another segment by the distal attachment means 93, and the remaining portion of the material, the flap portions, extending and terminating outboard of the proximal edges and preferably associated with the backsheet 42 by attachment means 88 to define the flaps.

The barrier cuffs and the flaps (backsheet 42) are adjoined together in any suitable manner. As used herein, the term "adjoined" encompasses configurations whereby the barrier cuffs are directly secured to the flaps by affixing portions of the barrier cuffs directly to the backsheet 42, and configurations whereby the barrier cuffs are indirectly joined to the flaps by affixing them to intermediate members which in turn are affixed to the backsheet 42. In a preferred embodiment, the barrier cuffs and the flaps are adjoined directly to each other in the diaper periphery 28 adjacent and outboard of the proximal edges by attachment means 88 and at the proximal edges by the edge attachment means 92 such as adhesive or any other attachment means such as heat/pressure sealing, ultrasonic bonding or any other methods as are known in the art. For example, a uniform continuous layer of adhesive, a patterned layer of adhesive, or an array of separate lines or spots of adhesive may be used. The attachment means 88 and the edge attachment means 92 are preferably a hot melt adhesive such as manufactured by Eastern Chemical Products Company of Kingsport, Tennessee and marketed under the tradename Eastobond A-3 or Century Adhesives, Inc. of Columbus, Ohio and marketed under the tradename Century 5227. (It should also be noted that the distal attachment means 93 herein are preferably the same type of means as the above attachment means.)

The edge attachment means 92 of the present invention for adjoining the proximal edges to the flaps provide a leakage-resistant seal along the proximal edge to present a barrier to the wicking of liquids through the topsheet so as to prevent liquids from wicking underneath the barrier cuffs to the edges of the diaper 20. In a preferred embodiment as shown in FIG. 1, 2, and 3, the edge attachment means 92 are positioned along the proximal edges preferably between the side edges 46 of the absorbent core 44 and the flap elastic members 60 in at least the crotch region 26 and between the waist edges 47 and the end edges 32 so that neither the topsheet 38 nor the absorbent core 44 extend beyond the proximal edges sure that liquids may not wick past the proximal edges and will be contained and held within the containment pocket.

The spacing means 76 for spacing the distal edges away from the liquid-receiving surface 40 is any member which gathers, contracts, stiffens, shortens or otherwise acts on the barrier cuffs so as to cause the barrier cuff to stand up to provide a channel 96 along the barrier cuff that acts as a constraint against the leakage of exudates. While any or all of the first and second barrier cuffs may have a spacing means associated with it, in a preferred embodiment, only the first barrier cuffs 62 have a spacing means 76 associated with them.

As shown in FIG. 1, the spacing means 76 preferably comprises a spacing elastic member 77 operatively associated with each of the first barrier cuffs 62 adjacent the first distal edge 66. The spacing elastic member 77 is preferably secured to the first barrier cuff 62 in an elastically contractible condition so that in a normally unrestrained configuration, the spacing elastic member 77 effectively contracts or gathers the first distal edge 66 of the first barrier cuff 62. The spacing elastic member 77 can be secured to the first barrier cuff 62 in an elastically contractible condition in at least two ways as is discussed in the above referenced U.S. Pat. No. 3,860,003 that issued to K. B. Buell.

The length of the spacing elastic member 77 in general is dictated by the diaper design. In the preferred embodiment illustrated in FIG. 1, the spacing elastic members 77 extend essentially the entire length of the barrier cuff 36 in the crotch region 26. In the most preferred embodiment, the spacing elastic members 77 extend longitudinally along the first distal edge 66 beyond the second distal edges 266 of the second barrier cuffs 262 (beyond the corner points 100) so as to cause not only the first barrier cuffs 62 but also the second barrier cuffs 262 to be spaced away from the liquid-receiving surface 40 of the diaper 20. The spacing elastic members 77 may extend beyond the second distal edges 266 any distance, including all the way to the end edges 32 of the diaper 20, so as to provide the most effective spacing of the second barrier cuffs 262 away from the liquid-receiving surface 40. (If a second spacing elastic member is alternatively associated with either or both of the second barrier cuffs 262, the spacing elastic member 77 may or may not extend beyond the second distal edges 266.)

As shown in FIG. 2, the spacing elastic member 77 is operatively associated with the first barrier cuff 62 by securing it within the first barrier cuff 62 with a spacing elastic attachment means 94. The spacing elastic attachment means 94 should be flexible and of sufficient adhesiveness to hold the spacing elastic member 77 in its stretched condition. While the spacing elastic members 77 may be secured to the barrier cuffs adjacent only the ends of the spacing elastic member 77, it is preferable to secure the entire length of the spacing elastic member 77 to the barrier cuffs. The spacing elastic attachment means 94 herein are preferably glue beads made of hot melt adhesive such as marketed by Findley Adhesives Incorporated, Elmgrove, Wisconsin, as Findley Adhesives 581, although the spacing elastic members 77 may be affixed to the barrier cuffs in any of several ways which are well known in the art. For example, the spacing elastic members 77 may be ultrasonically bonded or heat/pressure sealed into the barrier cuffs using a variety of bonding patterns or the spacing elastic members 77 may simply be glued to the barrier cuffs. A more detailed description of the manner in which the spacing elastic members 77 may be positioned and secured to the barrier cuffs can be found in U.S. Pat. No. 4,081,301, issued to Buell on March 28, 1978, and in U.S. Pat. No. 4,253,461, issued to Strickland and Visscher on March 3, 1981, both of which are incorporated herein by reference. It should also be noted that one or more spacing elastic members 77 can be used to elasticize each barrier cuff.

A spacing elastic member 77 which has been found suitable is an elastic strand having a cross section of 0.18 mm by 1.5 mm and made from natural rubber as available from Easthampton Rubber Company of Stewart, Virginia, under the trademark L-1900 Rubber Compound. Other suitable spacing elastic members 77 can be made from natural rubber, such as elastic tape sold under the trademark Fulflex 9411 by Fulflex Company of Middletown, Rhode Island. The spacing elastic member 77 may also comprise any heat shrinkable elastic material as is well known in the art. Other suitable elastic materials may comprise a wide variety of materials as are well known in the art include elastomeric films, polyurethane films, elastomeric foams and formed elastic scrim.

In addition, the spacing elastic members 77 may take a multitude of configurations. For example, the width of the spacing elastic members 77 may be varied; the spacing elastic members 77 may comprise a single strand or several parallel or non-parallel strands of elastic material; or the spacing elastic members 77 may be rectilinear or curvilinear.

The spacing means 76 for spacing the distal edges away from the liquid-receiving surface 40 may alternatively comprise several other elements. For example, the barrier cuffs may have stiffening means disposed in or on each barrier cuff. The stiffening means must be sufficiently stiff so that the distal edges are spaced away from the liquid-receiving surface 40. Suitable materials for the stiffening means include foams, nonwoven fabrics, batting, polyethylene film, formed films, spray glues, foamed elastomerics, polyester, polyurethane, or a high loft material as is manufactured by Carolina Formed Fabrics.

The spacing means 76 may also comprise means for shortening the length of the distal edges in comparison to the length of the edges of the diaper 20. The distal edges can be shortened by making a fold or pleat in the distal edges. This fold or pleat is secured by any of the holding means well known to those of ordinary skill in the art, such as adhesives or heat sealing. Alternatively, a section may be cut out of the distal edges and the resultant edges brought together to form a butt or lapp joint. The distal edges may also be shortened by attaching a length of the distal edge to the topsheet 38 at a position different from where the distal edge would lie when the diaper 20 is in a flattened out condition. Other shortening techniques as are known in the art may also be used.

The closing means 78 for securing the distal edges of the barrier cuffs together provide a more comfortable fit for the wearer and obviate inversion of the distal edges of the barrier cuffs during application and use. Inversion is generally defined as the inboard-disposed distal edges turning outwardly when the diaper 20 is applied to the wearer. In a preferred embodiment as shown in FIG. 1, the first distal edges 66 and the second distal edges 266 are secured together adjacent the corner points 100. While the distal edges need not be secured together, it is desirable that they be secured together so that the spacing function of the spacing elastic member 77 may be enhanced so as to space not only the first distal edges 66 but also the second distal edges 266 away from the liquid-receiving surface 40 and to insure a more liquid-tight containment pocket. In a preferred embodiment as shown in FIG. 1, such closing means 78 are disposed in the front waist region 22 and the back waist region 24 of the diaper 20 adjacent the corner points 100.

The closing means 78 are preferably adhesive beads consisting of hot melt adhesives such as marketed by Eastman Chemical Products Company, Kingsport, Tennessee, as Eastobond A-3 or Century Adhesives, Inc. of Columbus, Ohio as Century 5227 although other closing means as are known in the art such as ultrasonic bonding or heat/pressure sealing may also be used.

The diaper 20 is applied to a wearer by positioning the back waist region 24 under the wearer's back and drawing the remainder of the diaper 20 between the wearer's leg so that the front waist region 22 is positioned across the front of the wearer. The ends of the tape-tab fasteners 54 are then secured preferably to outwardly facing areas of the diaper 20. In this manner, the barrier cuffs should be disposed to provide the dispositions and functions described hereinbefore.

Basically, without intending to limit the present invention, the present invention is a diaper that is especially useful and leakage resistant against loose fecal material and gushes of urine, the improved containment characteristics being achieved in the following manner. As loose fecal material or urine is discharged onto the topsheet 38, some of the material flows or floats on the liquid-receiving surface 40 of the topsheet 38 (hereinafter referred to as surface material) and some of the material is absorbed by and wicks through the topsheet 38. The surface material moves from the point of discharge toward the longitudinal edges 30 and the end edges 32. Surface material will contact the barrier cuffs 10 along their inboard surface. In normal use, the surface material will tend to collect in the channels formed by the standing barrier cuffs; the material being held in the containment pocket until the diaper 20 can be removed. Improved containment is achieved because surface material would have to flow up the channel 96, which direction is substantially directly against the force of gravity in order to penetrate and flow over the distal edges of the barrier cuffs. Even should such material flow beyond the barrier cuffs, it should be retarded from leaking out of the diaper 20 by the gasketing effect achieved by the gasketing cuffs, as they draw and gather the flaps about the legs or the waist of the wearer, thereby providing a second and independent effective barrier against leakage so as to further prevent the soiling of adjacent garments. Liquids that are absorbed by and wicked through the topsheet 38 migrate toward the edges of the diaper 20. Because the topsheet terminates inwardly of the proximal edges and because a leakage-resistant seal is formed along the proximal edges, liquids will be generally prevented from wicking beyond the containment pocket.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A unitary disposable absorbent article comprising:
    an absorbent core having a garment surface, a body surface, side edges, and waist edges;
    a liquid impervious backsheet positioned adjacent said garment surface of said absorbent core;
    a liquid pervious topsheet positioned adjacent said body surface of said absorbent core;
    a side flap extending outwardly from and along each side edge of said absorbent core;
    an integral, liquid impermeable, first barrier cuff disposed adjacent each of said side flaps, each of said first barrier cuffs comprising a separate member joined to the absorbent article and having a first proximal edge and a first distal edge;
    first spacing means operatively associated with each of said first barrier cuffs for spacing said first distal edges upwardly away from said topsheet of the absorbent article;
    an integral second barrier cuff disposed along each end edge of the absorbent article, each of said second barrier cuffs comprising a separate member joined to the absorbent article and having a second proximal edge and a second distal edge;
    second spacing means operatively associated with each of said second barrier cuffs for spacing said second distal edges upwardly away from said topsheet of the absorbent article; and
    closing means for securing at least a portion of said first distal edges to said second distal edges.

2. The absorbent article of claim 1 wherein said spacing means comprises a spacing elastic member.

3. The absorbent article of claim 1 wherein said spacing means comprises multiple spacing elastic members.

4. The absorbent article of claim 1 wherein said second barrier cuffs are liquid impermeable.

5. The absorbent article of claim 1 wherein said first barrier cuffs are integral with said side flaps.

6. A unitary disposable absorbent article having a front waist region, a back waist region, and a crotch region, said absorbent article comprising:
    an absorbent core having a garment surface, a body surface, side edges, and waist edges;
    a liquid impervious backsheet positioned adjacent said garment surface of said absorbent core;
    a liquid pervious topsheet positioned adjacent said body surface of said absorbent core;
    a side flap extending outwardly from and along each side edge of said absorbent core in at least the crotch region;
    a liquid impermeable, integral first barrier cuff disposed adjacent each of said side flaps, each of said first barrier cuffs comprising a separate member joined to the absorbent article and having a first proximal edge and a first distal edge;
    first spacing means operatively associated with each of said first barrier cuffs for spacing said first distal edges upwardly away from said topsheet of the absorbent article;
    a waist flap extending outwardly from and along each waist edge of said absorbent core;
    a flap elastic member operatively associated with each of said waist flaps to thereby form second gasketing cuffs;
    an integral second barrier cuff disposed along each end edge of the absorbent article, each of said second barrier cuffs comprising a separate member joined to the absorbent article and having a second proximal edge and a second distal edge wherein said first distal edges and said second distal edges overlap at at least four corner points;
    second spacing means operatively associated with each of said second barrier cuffs for spacing said second distal edges upwardly away from said topsheet of the absorbent article; and
    closing means disposed adjacent each of said corner points for securing together said first distal edges and said second distal edges.

7. The absorbent article of claim 6 wherein said second barrier cuffs are liquid impermeable.

8. The absorbent article of claim 7 wherein each of said proximal edges of said second barrier cuffs are disposed inboard of said second flap elastic members.

9. The absorbent article of claim 8 additionally comprising edge attachment means for adjoining said first proximal edges to said side flaps to provide a seal along said first proximal edges.

10. The absorbent article of claim 9 wherein said first proximal edges are disposed outboard of said side edges of said absorbent core in at least the crotch region and said second proximal edges are disposed outboard of said waist edges of said absorbent core.

11. The absorbent article of claim 10 wherein said first spacing means comprises a spacing elastic member.

12. The absorbent article of claim 11 wherein said second spacing means comprises a spacing elastic member.

13. The absorbent article of claim 12 wherein said first spacing means comprises multiple spacing elastic members.

14. A unitary disposable absorbent article having a front waist region, a back waist region, and a crotch region, said absorbent article comprising:
- an absorbent core having a garment surface and a body surface;
- a liquid impervious backsheet positioned adjacent said garment surface of said absorbent core;
- a liquid pervious topsheet positioned adjacent said body surface of said absorbent core;
- a side flap extending outwardly from and along each side edge of said absorbent core;
- an integral, liquid impermeable, first barrier cuff disposed adjacent each of said side flaps along the longitudinal edges of the absorbent article, each of said first barrier cuffs comprising a separate member joined to the absorbent article and having a first proximal edge and a first distal edge;
- first spacing means operatively associated with each of said first barrier cuffs for spacing said first distal edges upwardly away from said topsheet of the absorbent article;
- an integral second barrier cuff disposed along at least one of the end edges of the absorbent article, said second barrier cuff comprising a separate member joined to the absorbent article and having a second proximal edge and a second distal edge, wherein said first distal edges and said second distal edges overlap at at least corner points;
- second spacing means operatively associated with each of said second barrier cuffs for spacing said second distal edges upwardly away from said topsheet of the absorbent article; and
- closing means disposed adjacent said corner points for securing together said first distal edges and said second distal edges.

15. The absorbent article of claim 14 wherein said second barrier cuff is positioned in the front waist region of the absorbent article.

16. The absorbent article of claim 14 wherein said second barrier cuff is positioned in the back waist region of the absorbent article.

* * * * *

UNITED STATES PATENT AND TRADEMARK OFFICE
CERTIFICATE OF CORRECTION

PATENT NO.    : 4,938,755

DATED         : July 3, 1990

INVENTOR(S)   : JOHN H. FOREMAN

It is certified that error appears in the above-identified patent and that said Letters Patent is hereby corrected as shown below:

Column 8, Line 3,          "hydrophillic" should read ---hydrophilic---.

Column 10, Line 11,        "attachments" should read ---attachment---.

Column 11, Line 42,        "an" should read ---and---.

Signed and Sealed this

Eighteenth Day of February, 1992

Attest:

HARRY F. MANBECK, JR.

*Attesting Officer*      *Commissioner of Patents and Trademarks*